(12) United States Patent
Cholet

(10) Patent No.: US 6,212,941 B1
(45) Date of Patent: Apr. 10, 2001

(54) PERMEAMETER WITH WIDE MEASUREMENT RANGE

(75) Inventor: Georges Cholet, Saran (FR)

(73) Assignee: Societe Nationale d'Exploitation Industrielle des Tabacs et Allumettes (FR)

( * ) Notice: Subject to any disclaimer, the term of this patent is extended or adjusted under 35 U.S.C. 154(b) by 0 days.

(21) Appl. No.: 09/234,837

(22) Filed: Jan. 22, 1999

(30) Foreign Application Priority Data

Jan. 22, 1998 (FR) .................................................. 98 00760

(51) Int. Cl.[7] .................................................. G01N 15/08
(52) U.S. Cl. .................................................. 73/38; 73/37
(58) Field of Search ............................ 73/37, 38, 152.05

(56) References Cited

U.S. PATENT DOCUMENTS

| | | | |
|---|---|---|---|
| 3,577,767 | * | 5/1971 | Stedile ..................................... 73/38 |
| 3,590,634 | * | 7/1971 | Pasternak et al. ..................... 73/159 |
| 3,839,899 | * | 10/1974 | McMillen ................................ 73/38 |
| 4,401,147 | * | 8/1983 | Beck et al. ............................ 162/263 |
| 4,480,463 | * | 11/1984 | Schumacher et al. ................... 73/38 |
| 4,495,795 | * | 1/1985 | Gupta ....................................... 73/38 |
| 4,513,603 | * | 4/1985 | Baillie .................................... 73/37 |
| 4,531,404 | * | 7/1985 | Phelps et al. ............................ 73/38 |
| 4,543,821 | * | 10/1985 | Davis, Jr. et al. ..................... 73/153 |
| 4,555,934 | * | 12/1985 | Freeman et al. ......................... 73/38 |
| 4,599,891 | * | 7/1986 | Brauer et al. ............................ 73/38 |
| 4,638,447 | * | 1/1987 | Odeh ................................... 364/556 |
| 4,718,270 | * | 1/1988 | Storr ....................................... 73/38 |

* cited by examiner

*Primary Examiner*—Hezron Williams
*Assistant Examiner*—David J. Wiggins
(74) *Attorney, Agent, or Firm*—William A. Drucker

(57) ABSTRACT

The permeameter embodying the invention comprises, on the one hand, a measuring head comprising two chambers opening onto two sides of the test piece, one of these chambers being connected to a measuring circuit successively comprising at least one flow meter and a pumping means capable of generating pressure or a partial vacuum in the circuit, an adjusting means being provided to maintain the circuit at a given pressure, and, on the other hand, an electronic circuit comprising plural calibrated amplifiers of which the inputs are connected to the output of the flow meter and of which the outputs are connected to the inputs of a multiplexer whose output is connected to a processor via an analog-to-digital converter.

The invention applies notably to the measurement of air permeability of cigarette paper.

7 Claims, 2 Drawing Sheets

PERMEAMETER WITH WIDE MEASUREMENT RANGE

BACKGROUND OF THE INVENTION

1. Field of the Invention

This invention relates to a permeameter, i.e. a device for the purpose of measuring the air permeability or fluid permeabilty of porous materials which can notably be in sheet form.

It applies particularly though not exclusively, to the measurement of the air permeability of cigarette papers, wrappers and/or oversleeves.

2. Description of the Prior Art

Generally, it is known that, in order to measure the permeability of a test piece which can consist of an object of any shape whatsoever, two opposite sides of this test piece are subjected to a difference in pressure so as to bring about, within the material included between these two sides, an air stream of which the flow rate is measured.

This difference in pressure is obtained either by generating a partial vacuum at one of the sides while bringing the other side to atmospheric pressure, or conversely, by subjecting one of the sides to air pressure while the other side is brought to atmospheric pressure.

The measurement of the flow of air passing through the test piece is then obtained by maintaining the partial vacuum or pressure applied to the test piece at a constant level, and by measuring by means of a flow meter, the flow of air circulating in the circuit and generating the partial vacuum or pressure as the case may be.

In compliance with ISO 2695 and CORESTA recommendation No. 40, the value VUC in CORESTA unit, (UC being equal to the flow of air ($cm^3$.min−1) passing through a 1 $cm^2$ surface of the test piece at a measuring pressure of 1 kPa), of the permeability at a given pressure can then be obtained from the following formula:

$$VUC = \frac{"Q(cm^3/mn)}{A(cm^2) \cdot d(kPa)"}$$

in which:
  d is the variance in pressure between the two sides of the test piece (usually 1 kPa)
  Q is the flow of air passing through a cross-section A of the test piece (usually 2 cm2) defined by the measuring head.

It so happens that the permeability of objects is very variable, as are therefore the air flows to be measured as a function of the test space area, the ambient test conditions and the applied pressure variance.

Moreover, it is frequently useful to measure, for the same test piece, the flow rate at two different pressures (or partial vacuums), usually 0.25 kPa and 1 kPa, with a view to determining a coefficient (called coefficient of ▌persillage▌) expressing the linearity of the flow/pressure characteristic.

Finally, it may be desirable to plot a graph of the flow/ pressure characteristics of the air flow passing through the test piece, especially with a view to determining the exact equation thereof.

Taking into account the fact that, in order to plot such a graph, the pressure (or partial vacuum) must necessarily be varied within a very wide range, the problem stemming from the narrowness of the measurement range of the flow meter is particularly acute. Hitherto, this problem made it necessary for the operator to step in to make scale changes. Total automation of this type of measurement was therefore not conceivable.

OBJECT OF THE INVENTION

The main object of this invention is to remedy the preceding disadvantages, particularly to provide a permeameter enabling such automation without any ensuing alteration of the measurement results.

SUMMARY OF THE INVENTION

Accordingly, there is provided a permeameter using a measuring head enabling the test piece to be at least partially imprisoned in an airtight manner, and comprising two chambers opening respectively onto two separate sides of the test piece, one of these chambers, known as the measurement chamber, being connected to a measuring circuit successively comprising at least one flow meter and a pumping means capable of generating pressure or a partial vacuum in the measuring circuit, an adjusting means being provided to maintain the circuit at a given pressure.

According to the invention, this permeameter is characterized in that it comprises an electronic circuit comprising a plurality of calibrated amplifiers of which the inputs are connected to the analog output of the flow meter and of which the outputs are connected to the respective inputs of a multiplexer driven by a processor. The output of this multiplexer is connected to an analog-to-digital converter of which the output is connected to the processor.

This processor is programmed so as to control both the multiplexer and a generator of set pressure values on the aforesaid adjusting means, and to compute the permeability of the object as a function of the pressure value and flow value it receives in digital form from the analog-to-digital converter.

According to one feature of the invention, the output voltage of the flow meter is applied to the input of a plurality of amplifiers.

By way of this arrangement, it becomes possible to measure, with an excellent degree of resolution, the flow detected in the measuring circuit for a very wide range of flow rates.

BRIEF DESCRIPTION OF THE DRAWINGS

An embodiment of the invention will now be described, by way of a non-limiting example, in reference to the corresponding accompanying drawings in which.

DESCRIPTION OF THE PREFERRED EMBODIMENTS

Figure 1:
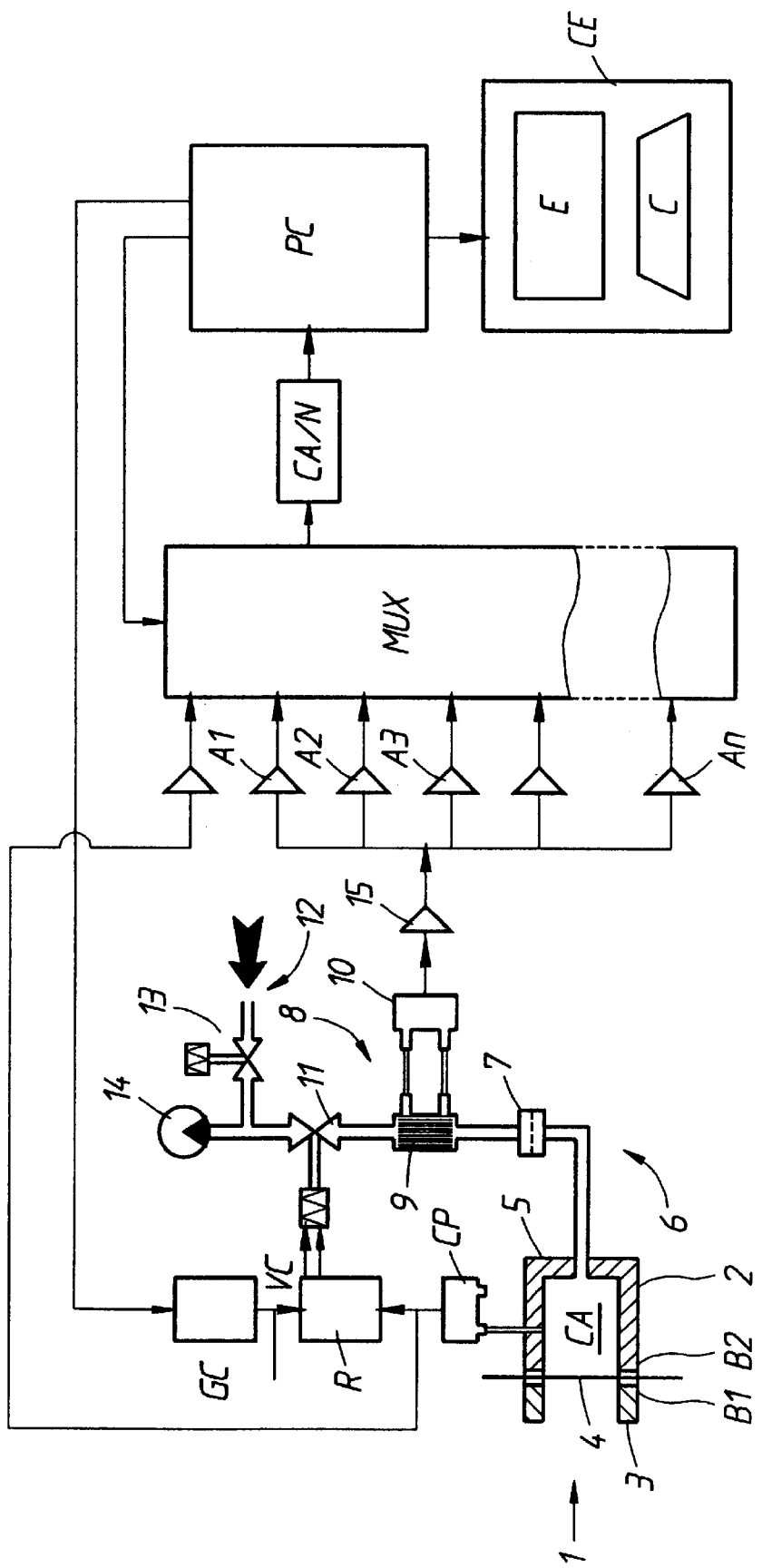
FIG. 1 is a theoretical diagram of an automatic permeameter enabling quick, accurate measurement of the permeability of sheets of paper.

In this example, the permeameter comprises a measuring head 1 comprising two cylindrical tubular parts 2, 3 of substantially same diameter, mobile in relation to one another and susceptible of being arranged coaxially in relation to one another in order to abut against one another whilst clasping, between their radial annular edges $B_1$, $B_2$, a sheet of paper 4 which in this instance constitutes the test piece of which the permeability is to be measured. These radial annular edges $B_1$, $B_2$ can be coated with a lining enabling good tightness to be ensured between the two parts 2, 3 of the head 1 and the sheet of paper 4. The tubular part 3 is open at both its ends, while the tubular part 2 comprises a bottom 5 situated on the side opposite the edge $B_1$ so as to delimit a suction chamber CA that is closed off by the sheet 4.

This chamber CA communicates with a suction pipe 6 successively comprising:

a filter 7 for the purpose of preventing particles of material being sucked into the suction pipe and thus disrupting measurement;

a flow meter 8 comprising partial vacuum generating device 9 mounted in series with the suction pipe 6 and a pressure sensor 10 measuring the difference in pressure between the input and output of this partial vacuum generating device 9;

a control electrovalve 11;

a circuit for bringing the suction pipe and pneumatic circuit to atmospheric pressure 12 controlled by an electrovalve 13; and a suction pump 14 (or any other vacuum generator).

The pressure inside the chamber CA is measured by a pressure sensor CP connected, by its output, to an analog-to-digital converter CA/N and to an automatic control circuit R which controls the electrovalve 11 as a function of the difference between the value of the pressure measured by the sensor CP and a set value VC imposed by an analog-to-digital converter CA/N GC driven by the processor PC in accordance with a measurement program.

The analog signal supplied by the pressure sensor 10 is applied, after filtering and pre-amplification (pre-amplifier 15), to the inputs of a plurality of calibrated amplifiers $A_1$, $A_2$, $A_3$, $A_n$ of which the outputs are connected to respective inputs of a multiplexer MUX driven by a processor PC.

The output of this multiplexer MUX is connected to the input of an analog-to-digital converter CA/N which successively transmits, to the processor PC, the digital values corresponding to the voltages supplied by the amplifiers $A_1 \ldots A_n$.

The processor PC is coupled with a keyboard/screen console CE and is connected to the set value generator GC associated with the automatic control circuit R.

Figure 2:
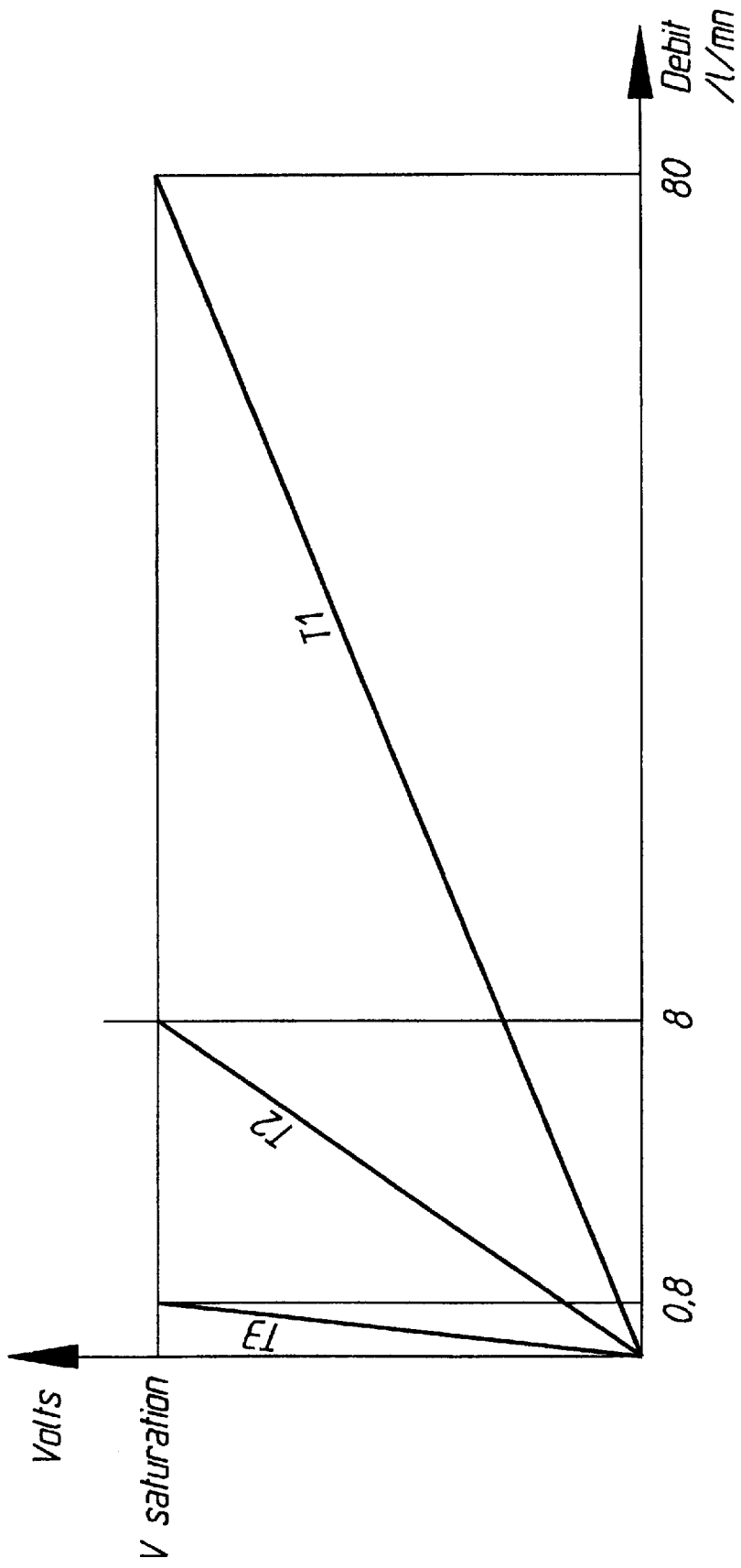
FIG. 2 is a voltage/flow rate diagram representing curves showing the output variation of the calibrated amplifiers provided at output of the flow meter of the permeameter represented in FIG. 1.

The working of this device is illustrated in FIG. 2 which comprises a diagram showing a curve of the variation in voltage at output of the amplifiers $A_1 \ldots A_n$ according to flow rate. In this diagram, the curves $T_1$, $T_2$, $T_3$ correspond respectively to the voltages supplied by the amplifiers $A_1$, $A_2$, $A_3$. The gains of these amplifiers are respectively 1, 10 and 100.

Under the control of, the processor PC, the multiplexer MUX successively applies the output voltages of the amplifiers $A_1$, $A_2$, $A_3$ to the input of the analog-to-digital converter CA/N, though at any given moment, only the highest of these output voltages below the saturation voltage will be taken into consideration.

As previously mentioned, the processor PC controls the set values of the pressure control circuit R. Thus, the processor will be able to plot the pressure/flow rate curve on the screen E or on a printer by ordering a sequence comprising a succession of cycles each including the following, working from a minimum set pressure value:

a incrementation Δp of the set pressure value, a stabilizing of the newly acquired pressure value, analog measurement of the flow rate, determination of the digital value of the flow rate by multiplexing of the output voltages of the amplifiers $A_1 \ldots A_n$ with analog-to-digital conversion of said voltages, and correction, if necessary, of the results in order to factor in variations in gain between the amplifiers $A_1 \ldots A_n$, analog measurement of the real pressure, determination of the digital value of the pressure by analog-to-digital conversion, storage of the measured pressure/flow rate couple in a memory associated with the processor PC.

Of course, when all the flow rate/pressure couples corresponding to the pressure variation range of the pressure/flow rate curve to be plotted have been stored in the memory, the processor PC can then plot the curve on the screen on by means of the printer and can compute the permeability according to the previously stated formula as well as the coefficient of "persillage" characterizing the flow rate/pressure relation in accordance with the following process:

the successive establishing, in the chamber CA, of pressures of 0.25 kPA and 1.00 kPa;

the storing in the memory of the respective air flow rates $Q_1$ and $Q_2$ ($cm^3$ $min^{-1}$) measured in respect of these two pressures;

computation of the ratio Y by means of the following formula:

$$Y=(Q_1/Q_2)\times(1.0/0.25)$$

repetition of this procedure for further test pieces and calculation of the average of the values obtained for Y;

if the average value of Y is no more than 2% off the value 1.00 (i.e. if, in practice, it does not exceed 1.02), the flow rate/pressure relation will be deemed linear;

should it so happen that the material tested has non-linear characteristics, the measurement of the air flow for a single pressure difference is not sufficient to characterize the material. The air flow should also be determined by using the second pressure difference of 0.25 kPa.

Typically, the device disclosed above can comprise three sequences of automatic air flow measurement:

| | |
|---|---|
| 0 → 800 $cm^3$/mn | resolution: 0.3 $cm^3$/mn |
| 800 → 8,000 $cm^3$/mn | resolution: 3 $cm^3$/mn |
| 8,000 → 80,000 $cm^3$/mn | resolution: 30 $cm^3$/mn |

The adjustment, of the test piece pressure being included between 0 and 2 kPa to a pressure accuracy of 0.001 kPa.

This device can have three types of operating modes:

measurement for one single partial vacuum value (usually 1 kPa);

measurement at two successive partial vacuum values (usually 1 kPa and 0.25 kPa) with computation of the coefficient of "persillage";

plotting of the flow rate/pressure curve (pressure ranging from 0 to 2 kPa) with computation of the coefficient of "persillage".

What is claimed is:

1. Permeameter of a fluid driven type comprising a measuring head enabling a test piece with at least 2 sides thereof to be at least partially imprisoned in an airtight manner, this measuring head comprising a pair of chambers opening respectively onto said sides of the test piece, one of these chambers being connected to a measuring circuit successively comprising a series connection of at least one analog output flow meter for measuring a fluid flow value or a fluid flow rate from said test piece and a pumping means capable of generating pressure or a partial vacuum upon said test piece at a certain pressure value in the measuring circuit, a pressure sensor and, an adjusting means being provided to maintain the measuring circuit at a given pressure or partial vacuum, wherein said measuring circuit comprises an electronic circuit comprising a plurality of calibrated amplifiers of which the inputs are connected to the analog output(s) of the flow meter(s) and of which the amplifier outputs are connected to respective inputs of an analog output multiplexer driven by an electronic processor, the analog output of this multiplexer being connected to an analog-to-digital converter of which the A/D converter output is connected to the processor for automated determination of a set of permeability results obtained for said test piece in terms of a digital flow rate value.

2. Permeameter as claimed in claim 1, wherein the processor is programmed to control both the multiplexer and a generator of set pressure values on the aforesaid adjusting means.

3. Permeameter as claimed in claims 1, wherein that the processor is programmed to compute the permeability of the test piece as a function of a pressure value established in the measurement chamber and the flow value it receives in digital form from the analog-to-digital converter.

4. Permeameter as claimed in claim 1, wherein in that said plurality of amplifiers have a corresponding plurality of saturation voltages and amplifier output voltages and where also the processor instructs the multiplexer to successively apply output voltages of the amplifiers to the input of the analog-to-digital converter, and, at all times, only takes into consideration the highest of these output voltages below a saturation voltage of said amplifiers.

5. Permeameter as claimed in claim 2, wherein the said set pressure value generator is driven by the processor.

6. Permeameter as claimed in claim 5, wherein the processor is programmed to plot a set of corresponding pressure value/flow rate value data into a curve by way of a sequence comprising a succession of cycles each including the following, working from a minimum set pressure value:

an incrementation of a set pressure value as applied upon said test piece, a stabilizing of the pressure and acquisition of the pressure value thereof, analog measurement of the flow rate induced across said test piece, determination of a digital value of the flow rate by multiplexing of the output voltages of the amplifiers with analog-to-digital conversion of said voltages, and correction, if necessary, of results in order to factor in variations in a set of gain factors between the different amplifiers, storage of the measured pressure/flow rate as a set of coupled parameter values in a memory associated with the processor.

7. Permeameter as claimed in claim 1 applied for testing a plurality of distinct test pieces by using a programmed mathematical process, wherein the processor computes a system value for a coefficient of "persiflage" characterizing the determination of a flow rate/pressure relation in accordance with a following process:

the successive establishing, in the chamber, of pressures of 0.25 kPA and 1.00 kPa;

the storing in the memory of the respective air flow rates $Q_1$ and $Q_2$ ($cm^3$ $min^{-1}$) measured;

computation of the ratio Y by means of the following formula:

$$Y=(Q_1/Q_2)\times(1.0/0.25)$$

repetition of this procedure for each of several test pieces to be air-flow tested in sequence, and calculation of the average of the values obtained among the several test pieces for a mean value Y that will enable judgement towards whether the test pieces manifest a linear characteristic in said flow rate/pressure relation.

* * * * *